United States Patent
Alas (10) Patent No.: US 8,181,786 B1
(45) Date of Patent: May 22, 2012

(54) DENTAL CARE KIT AND PROMOTIONAL METHOD THEREOF

(76) Inventor: Abdulrahman Alas, Bakersfield, CA (US)

(*) Notice: Subject to any disclaimer, the term of this patent is extended or adjusted under 35 U.S.C. 154(b) by 0 days.

(21) Appl. No.: 13/066,983

(22) Filed: Apr. 28, 2011

(51) Int. Cl.
*A61B 19/02* (2006.01)
(52) U.S. Cl. ........................ 206/570; 206/63.5
(58) Field of Classification Search .............. 206/363, 206/364, 365, 366, 367, 368, 369, 370, 570, 206/571, 63.5
See application file for complete search history.

(56) References Cited

U.S. PATENT DOCUMENTS

| | | | | |
|---|---|---|---|---|
| 3,921,649 A | * | 11/1975 | Milbrath | 132/308 |
| 4,293,074 A | * | 10/1981 | Dunsky | 206/572 |
| 5,501,602 A | * | 3/1996 | Anderson et al. | 434/263 |
| 6,461,164 B1 | * | 10/2002 | Ramelli | 434/263 |
| 2006/0110701 A1 | * | 5/2006 | Cwik | 433/31 |
| 2006/0289030 A1 | * | 12/2006 | Pho | 132/309 |
| 2008/0227051 A1 | * | 9/2008 | Szwajkowski et al. | 433/24 |

* cited by examiner

*Primary Examiner* — Jacob K Ackun
(74) *Attorney, Agent, or Firm* — Raymond Y. Chan; David and Raymond Patent Firm (57) ABSTRACT

A dental care promotional kit includes a housing, a dental care set, and a promotion tool. The housing has a receiving cavity, a reflective windows formed on one of the front promotional panel and the rear promotional panel, and at least one promotional zone formed on the housing. The promotion tool is retrievably disposed in the receiving cavity of the housing, and comprises a promotional member and a reflective element attached on the promotional member, wherein the promotional member further has a promotional section formed thereon for allowing promotional materials to be printed on the promotional section, and is capable of being taken out from the receiving cavity, such that a user is able to freely retrieve the dental care set for performing basic dental care while being imparted with business goodwill shown on the promotion tool and the promotional zone.

10 Claims, 6 Drawing Sheets

DENTAL CARE KIT AND PROMOTIONAL METHOD THEREOF

BACKGROUND OF THE PRESENT INVENTION

1. Field of Invention

The present invention relates to a dental care kit, and more particularly to a dental care kit with a promotion tool which allows a user to perform basic dental care while being exposed to predetermined promotional materials.

2. Description of Related Arts

A conventional dental care kit usually comprises a kit casing and a plurality of dental care accessories, such as toothpaste, a mini toothbrush, dental floss, or the likes. When a user wishes to use any of these dental care accessories, he or she needs to take out the corresponding dental care accessory and use it. Very often, the dental care kit is stored at home so that when the user eats in a restaurant, the user can only use the accessories when he or she goes back home.

Furthermore, the conventional dental care kit as mentioned above is usually branded so that all of the accessories contained in the kit casing come from the same brand. This is so because the dental care kit represents a product of that brand and the corresponding company wishes to sell all the accessories contained in the dental care kit as a combo. Users no longer need to buy individual accessories one by one.

As a result, the above mentioned dental care kit is seldom a souvenir distributed by restaurants. Even if it is, conventional dental care kits are seldom the tool for extensive marketing. The reason for this may be that manufacturers of such dental care kit tend to think that dental care accessories are something which is rapidly disposable and no one will really pay attention to what is contained in those accessories. Furthermore, since the accessories are perceived to be disposed of very rapidly, business strategy may actually determine that the marketing value of such dental care accessories is at best minimal.

SUMMARY OF THE PRESENT INVENTION

The invention is advantageous in that it provides a dental care kit with a promotion tool which allows a user to perform basic dental care right after eating while being exposed to predetermined promotional materials.

Another advantage of the invention is to provide a dental care kit with a promotion tool, wherein the dental care kit or one of the dental care accessories is designed to be kept by the user for a prolonged period of time so as to maximum the marketing value of the dental care kit because the user of the present invention will come into contact with promotional materials for the corresponding extended period of time.

Another advantage of the invention is to provide a dental care kit with a promotion tool which can be made of inexpensive materials so as to minimize the manufacturing cost of the present invention. In other words, the dental care kit of the present invention can best be made as a free souvenir with extensive and substantial marketing ability.

Another advantage of the invention is to provide a dental care kit with a promotion tool, wherein the healthy image of the dental care kit is capable of substantially boosting the marketing effect of the promotion tool while also promoting a healthy habit on the part of the users of the present invention.

Additional advantages and features of the invention will become apparent from the description which follows, and may be realized by means of the instrumentalities and combinations particular point out in the appended claims.

According to the present invention, the foregoing and other objects and advantages are attained by providing a dental care promotional kit for immediate use after eating, comprising:

a housing having a front promotional panel, a rear promotional panel, a receiving cavity defined between the front promotional panel and the rear promotional panel, a see-through window formed on one of the front promotional panel and the rear promotional panel, and at least one promotional zone formed on the housing a dental care set retrievably disposed in the receiving cavity for providing basic dental care to a user; and a promotion tool which is retrievably disposed in the receiving cavity of the housing, and comprises a promotional member and a reflective element attached on the promotional member, wherein the promotional member further has a promotional section formed thereon for allowing promotional materials to be printed on the promotional section, and is capable of being taken out from the receiving cavity, such that a user is able to freely retrieve the dental care set from the receiving cavity for performing basic dental care after eating while being imparted with business goodwill shown on the promotion tool and the promotional zone of the housing.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Referring to FIG. 1 to FIG. 4 of the drawings, a dental care promotional kit for immediate use after eating according to a preferred embodiment of the present invention is illustrated, in which the dental care promotional kit comprises a housing 10, a dental care set 20, and a promotion tool 30.

Figure 1:
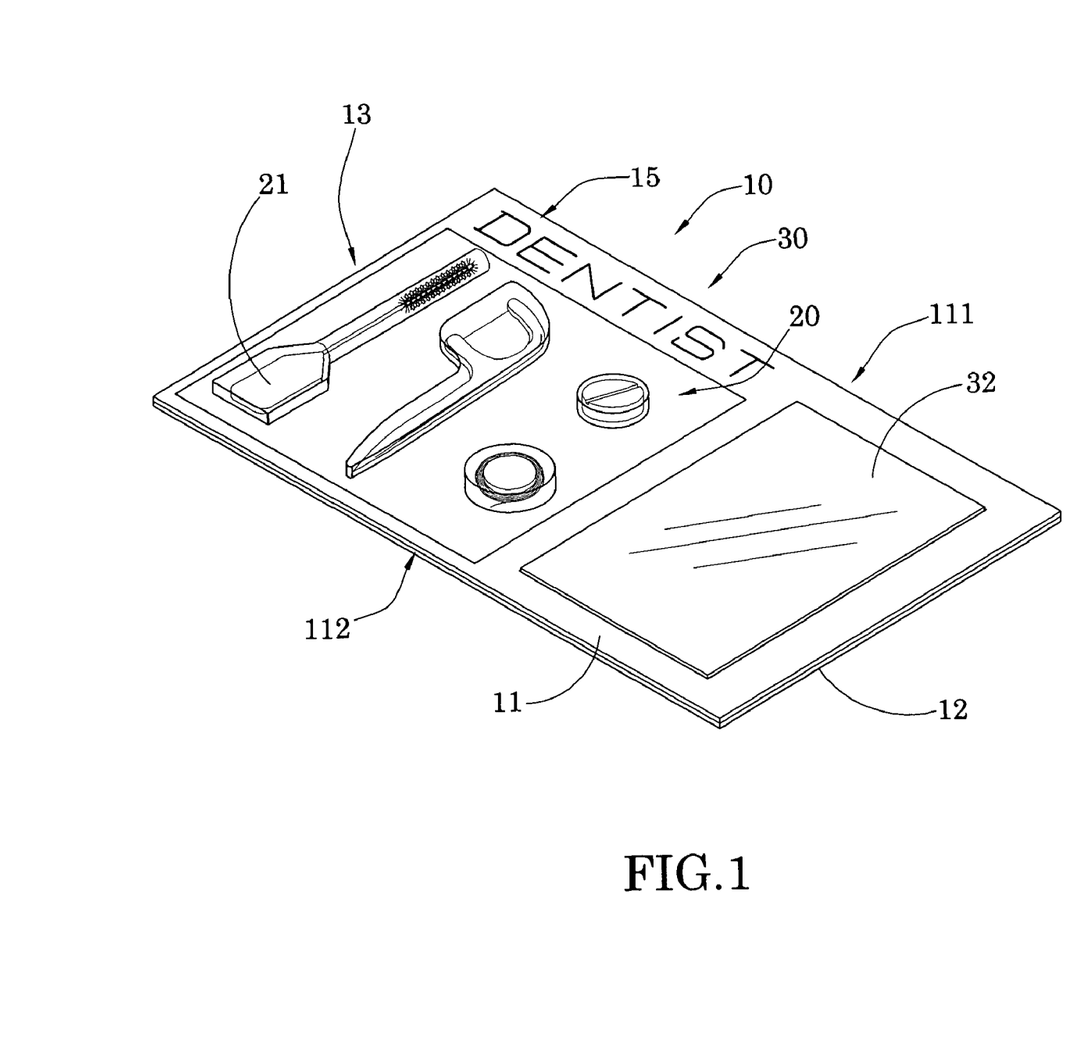
FIG. 1 is a perspective view of a dental care kit according to a preferred embodiment of the present invention.
Figure 2:
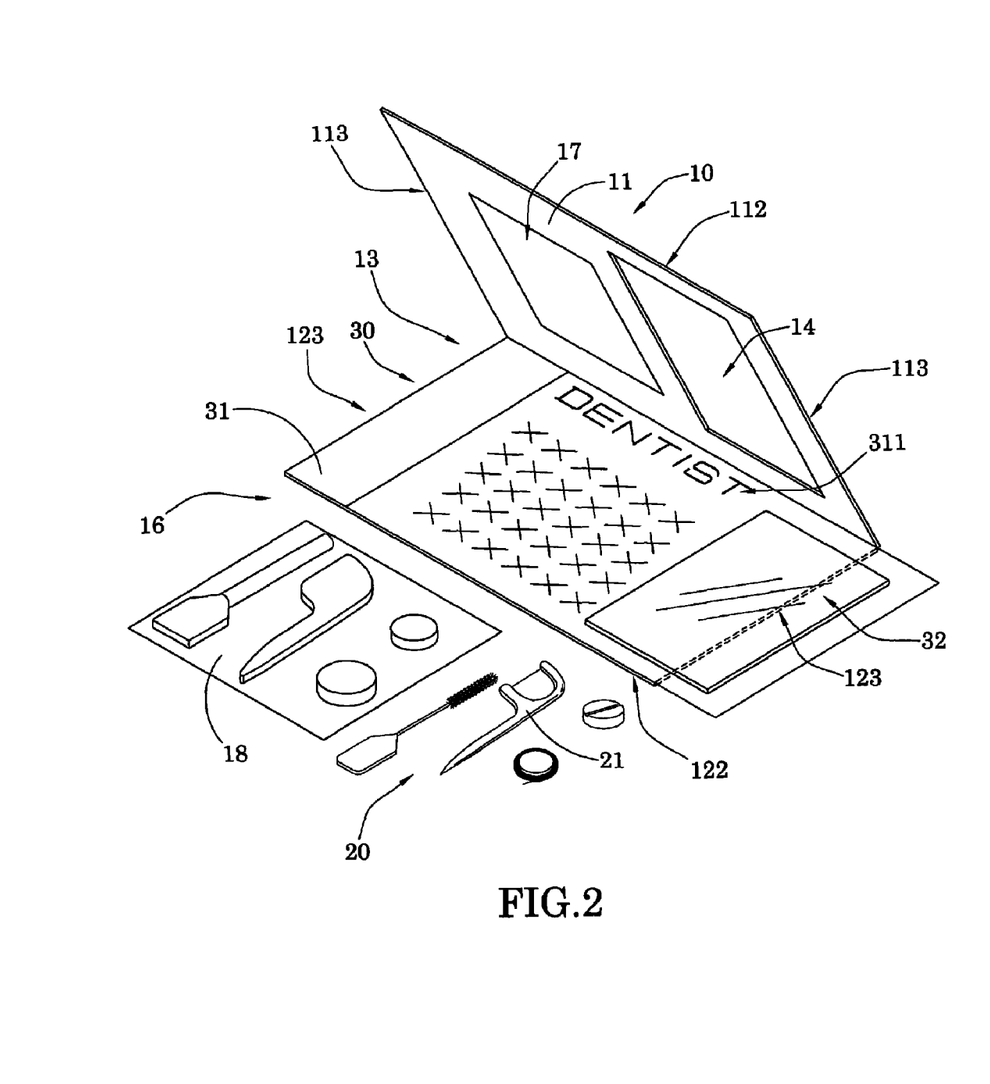
FIG. 2 is an exploded perspective view of the dental care kit according to the above preferred embodiment of the present invention.

The housing 10 has a front promotional panel 11, rear promotional panel 12, a receiving cavity 13 defined between the front promotional panel 11 and the rear promotional panel 12, a see-through window 14 formed on one the front promotional panel 11 or the rear promotional panel 12 (but preferably on the front promotional panel 11), and the least one promotional zone 15 formed on the housing 10.

The dental care set 20 is retrievably disposed in the receiving cavity 13 for providing basic dental care to a user whenever the user retrieve the dental care set 20 from the receiving cavity 13.

Figure 3:
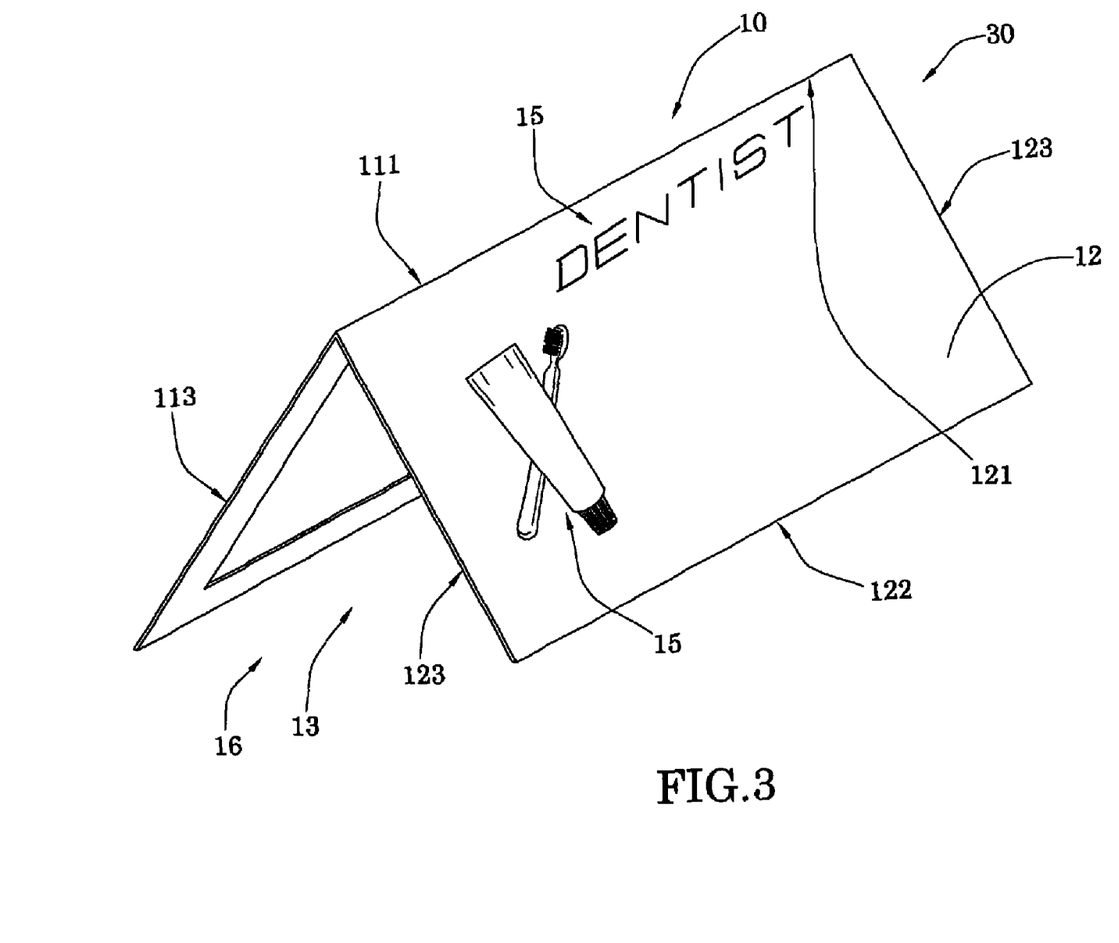
FIG. 3 is an exploded perspective view of a promotion tool of the dental care kit according to the above preferred embodiment of the present invention.

The promotion tool 30 is retrievably disposed in the receiving cavity 13 of the housing 10, and comprises a promotional member 31 and a reflective element 32 attached on the promotional member 31, wherein the promotional member 31 further has a promotional section 311 formed thereon for allowing promotional materials to be printed on the promotional section 311, and is capable of being taken out from the receiving cavity 13, such that a user is able to freely retrieve the dental care set 20 from the receiving cavity 13 for performing basic dental care after eating while being imparted with business goodwill shown on the promotion tool 30 and the promotional zone 15 of the housing 10.

According to the preferred embodiment of the present invention, the housing 10 is made of light-weight, flexible, durable and inexpensive material so that the user can be able to retrieve the promotion tool 30 and the dental care set 20 with ease, while the manufacturing cost of the present invention can be kept to the minimum. As such, the housing 10 is preferably made of paper material, such as cardboard material. As shown in FIG. 1 of the drawings, the housing 10 is crafted and designed to have a rectangular cross section. However, it is worth mentioning that the housing 10 can be made to have any other cross sectional shapes.

The front promotional panel 11 has a first top edge 111, a first bottom edge 112, and a plurality of first side edges 113, while the rear promotional panel 12 has a second top edge 121, a second bottom edge 122, and a plurality of second side edges 123, wherein the first top edge 111 and the second top edge 121 are integrally formed while the first bottom edge 112 and the second bottom edge 112 are inwardly folded along the corresponding top edges 111, 121 respectively so that a user is able to flip the housing 10 along the first and the second top edges 111, 121 for accessing the receiving cavity 13. In other words, the receiving cavity 13 is defined between the front promotional panel 11 and the second promotional panel 12 and the user is able to easy access the receiving cavity 13 by unfolding the first and the second promotional panels 11, 12.

Figure 5:
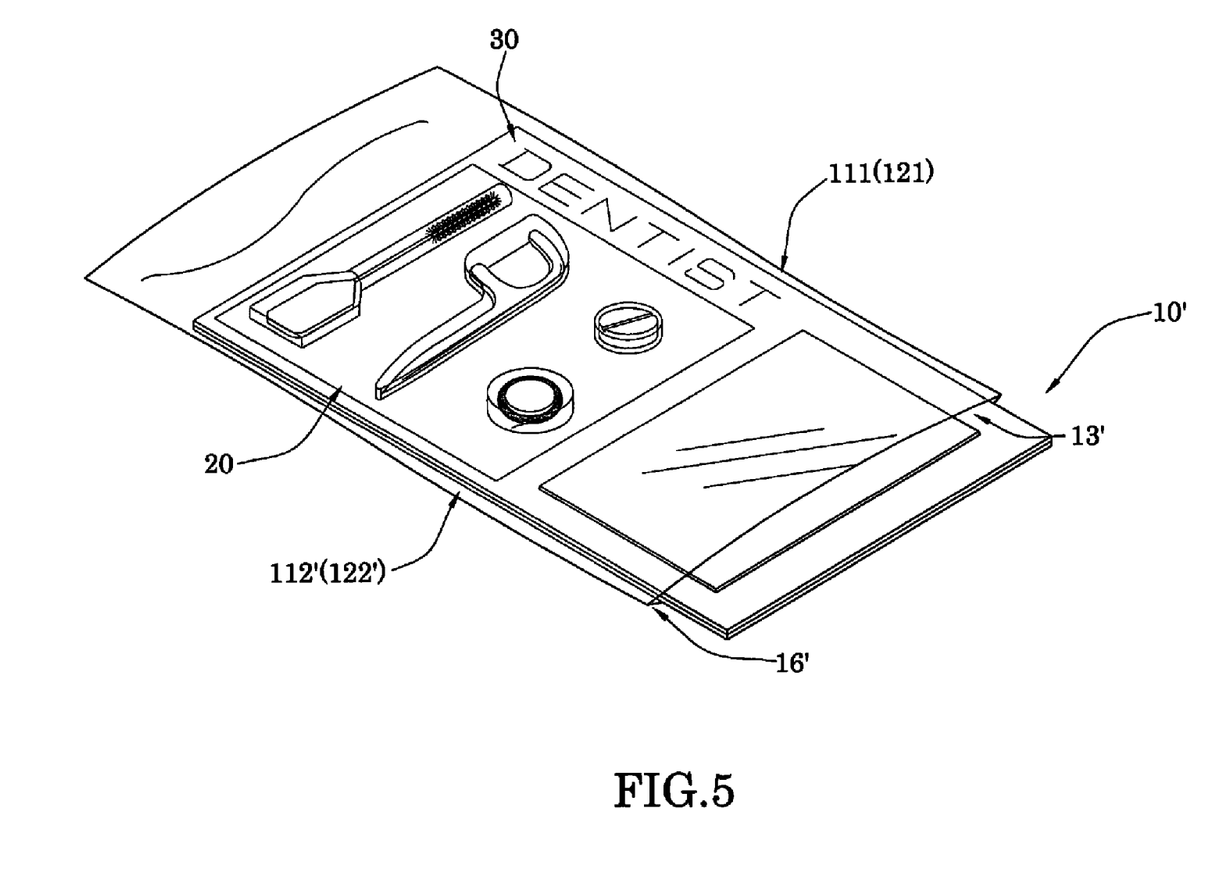
FIG. 5 is a first alternative illustration of the dental care kit according to the above preferred embodiment of the present invention.

Alternatively, as shown in FIG. 5 of the drawings, the first bottom edge 112' and the second bottom edge 122' can also be integrally formed so that the user can only access the receiving cavity 13' through side openings of the housing 10'. In other words, the housing 10' further has at least one opening 16' formed thereon for communicating the receiving cavity 12 with an exterior of the housing 10'. The opening can be side opening, or bottom opening. Where the housing 10' has a plurality of openings 16', they are formed as side openings and bottom opening of the housing 10 (as shown in FIG. 1 of the drawings).

Figure 6:
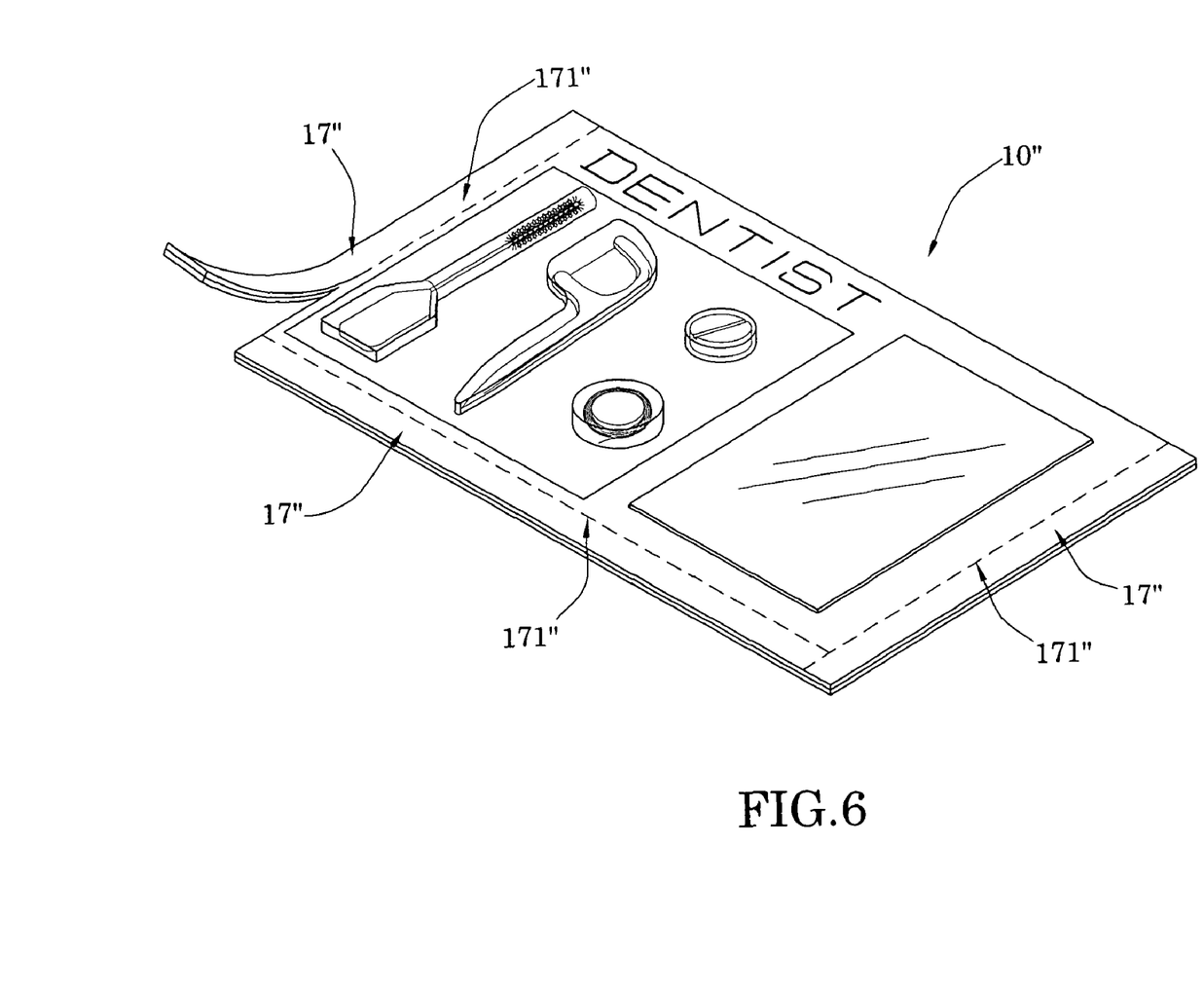
FIG. 6 is a second alternative illustration of the dental care kit according to the above preferred embodiment of the present invention.

As a second alternative, as shown in FIG. 6 of the drawings, the housing 10" further has a plurality of attachment edge portions 17" formed along the first bottom edge 112, the first side edges 113, the second bottom edge 122, and the second side edges 123, wherein the attachment edge portions 17" are arranged to be torn by the user along perforated lines 171" for unfolding the front promotional panel 11 and the rear promotional panel 12.

The see-through window 14 of the housing 10 is for allowing the user to use the reflective element 32 of the promotion tool 30. Thus, the reflective element 32 is normally disposed in the receiving cavity 12 at a position aligned with the see-through window 14 so that the reflective element 32 is exposed to the exterior of the housing 10 for allowing user to see his or her reflective image on the reflective element 32.

The promotional zone 15 is printed promotional or advertising materials such that a user of the present invention may directly receive such information when he or she carries the dental care kit of the present invention, or when he or she tries to access the retrieve the dental care set 20 from the receiving cavity 12. One feature of this promotional zone 15 is that the advertising or promotional materials printed thereon need not come from the manufacturer of the dental care set 20. Rather, any one or organization may arrange for the advertisement to be printed onto the promotional zone 15. Note that the housing 10 may comprise a plurality promotional zones 15 formed on the front promotional panel 11 and the rear promotional panel 12 wherein each of the promotional zones 15 contains advertising materials of different parties or organizations. As such, a single dental care kit of the present invention allows different parties or organization to subscribe one or more promotional zones 15 to advertise their business.

The housing 10 further comprises an illustrative window 17 formed on the front promotional panel 11 at a position aligned with the dental care set 20. In other words, the dental care set 20 is visible from an exterior of the housing 10 through the illustrative window 17. In addition, the housing 10 further comprises a protective rack 18 mounted in the receiving cavity 13 for securely supporting the dental care set 20 in position. According to the preferred embodiment of the present invention, the protective rack 18 is transparent and is mounted within the receiving cavity 13 to provide a cover to the illustrative window 17 so as to protect the dental care set 20 from being directly accessible from an exterior of the housing 10 through the illustrative window 17, while allowing the user of the present invention to visually observe the dental care set from the exterior of the housing 10 through the illustrative window 17.

It is worth mentioning that the illustrative window 17 and the reflective window 14 are next to each other so that a user may be able to discern the reflective image of his or her own while deciding which constituent of the dental care set 20 is best available for him or her.

The dental care set 20 comprises a plurality of dental care accessories 21 spacedly supported at the receiving cavity 13 for performing a wide range of dental care procedures for the user of the present invention. For example, the dental care accessories 21 may include a toothpick, a mini toothbrush, a small spool of dental floss, teeth whitening agent, and the likes. It is worth mentioning that each of the dental care accessories 21 is securely supported in the receiving cavity 13 by the protective rack 18 which makes all the dental care accessories 21 visually accessible from the exterior of the housing 10 while being physically protected by the protective rack 18. Retrieval of the dental care accessories 21 and the protective rack 18 from the receiving cavity 13 must be through the opening 16 formed on the housing 10.

Thus, the protective rack 18 further has a plurality of protective compartments 181 indently and spacedly formed thereon, wherein each of the dental care accessories 21 is fittedly received in the corresponding protective compartment 18 so as to be securely mounted and protected within the receiving cavity 13.

On the other hand, the promotional member 31 of the promotion tool 30 is also made of light-weight material so as to allow easy carrying and inexpensive manufacturing. It is preferably made of paper material such as the paper used for manufacturing a business card. Promotional or marketing materials are printed on the promotional section 311 of the promotional member 31 while the reflective element 32 is attached on the promotional member 31 such that when the promotional member 31 is taken out from the receiving cavity 13, the reflective element 32 is still attached on the promotional member 31 for providing reflective image to the user.

It is worth mentioning that the reflective element 32 is a mirror in this preferred embodiment for providing a relatively clear reflective image of the user. The user may then use the reflective element 32 while using any one of the dental care accessories 21. This provides an extremely convenient way of accommodating the user's need after he or she has eaten. Furthermore, the dental care kit is also suitable for being placed next to a setting when the user is enjoying his or her meal.

Alternatively, the reflective element 32 may also take the form of a metallic sheet having a shiny or semi-shiny reflective surface (such as a thin aluminum sheet) attached onto promotional member 31 for reflecting the user's image when he or she looks at the reflective element 32.

Figure 4:
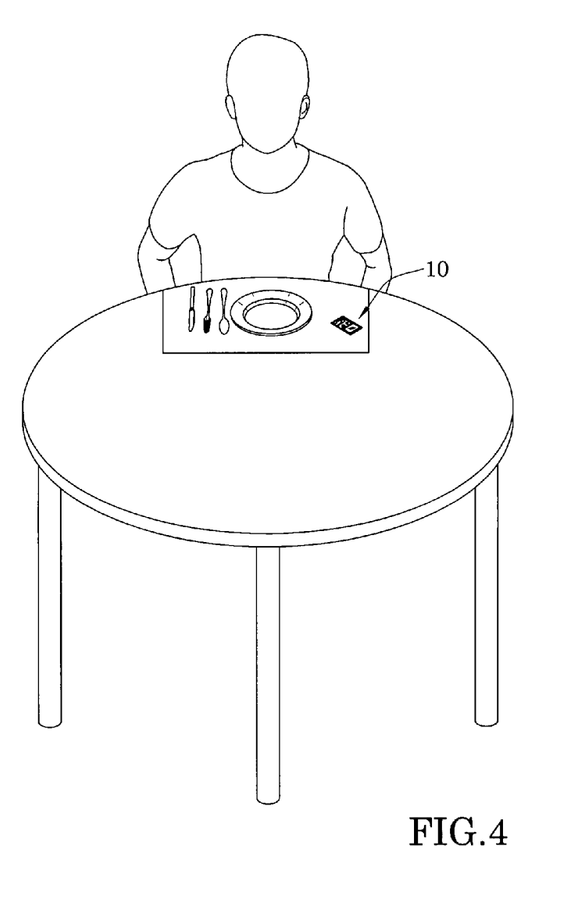
FIG. 4 is a schematic diagram of the dental care kit according to the above preferred embodiment of the present invention.

The operation of the present invention is as follows: as shown in FIG. 4 of the drawings, the dental care kit may first be put on a dining table. When the user finishes eating, he or she may simply hold the housing 10 for a quick glimpse of his or her face by using the reflective element 32. When the user wishes to use any one of the dental care accessories 21, he or she may take out the protective rack 18, the dental care kit 20, as well as the promotion tool 30. After that, the user can use any one of the dental accessories 21. It is important to mention that the user may keep the promotion tool 30, i.e. the promotional member 31 and the reflective element 32 for an extended period of time because the reflective member 32, which is attached onto the promotional member 31, can be reused. When the user keeps the promotion tool 30 for an extended period of time, the advertising or promotional materials will be imparted to the user for the same extended period of time and this effectively increases the business goodwill of those who put the advertising or promotional materials onto the dental care kit of the present invention. Moreover, since the dental care kit represents a positive and healthy lifestyle, the image of the advertising or promotional materials will be further boosted up.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A dental care promotional kit for immediate use after eating, comprising:

a housing having a front promotional panel, a rear promotional panel, a receiving cavity defined between said front promotional panel and said rear promotional panel, a see-through window formed on one of said front promotional panel and said rear promotional panel, and at least one promotional zone formed on said housing;

a dental care set retrievably disposed in said receiving cavity for providing basic dental care to a user; and a promotion tool which is retrievably disposed in said receiving cavity of said housing, and comprises a promotional member and a reflective element attached on said promotional member, wherein said promotional member further has a promotional section formed thereon for allowing promotional materials to be printed on said promotional section, and is capable of being taken out from said receiving cavity, such that a user is able to freely retrieve said dental care set from said receiving cavity for performing basic dental care after eating while being imparted with business goodwill shown on said promotion tool and said promotional zone of said housing;

wherein said front promotional panel has a first top edge, a first bottom edge, and a plurality of first side edges, while said rear promotional panel has a second top edge, a second bottom edge, and a plurality of second side edges, wherein said first top edge and said second top edge are integrally formed while said first bottom edge and said second bottom edge are inwardly folded along said corresponding top edges respectively so that a user is able to flip said housing along said first and said second top edges for accessing said receiving cavity;

wherein said reflective element is normally disposed in said receiving cavity at a position aligned with said see-through so that said reflective element is exposed to an exterior of said housing for allowing user to see reflective image on said reflective element;

wherein said promotional zone is printed with promotional materials such that a user is able to directly receive said promotional materials when using said dental care promotional kit;

wherein said housing further comprises an illustrative window formed on said front promotional panel at a position aligned with said dental care set, so that said dental care set is visible from an exterior of said housing through said illustrative window;

wherein said housing further comprises a protective rack mounted in said receiving cavity for securely supporting said dental care set in position, wherein said protective rack is transparent and mounted within said receiving cavity to provide a cover to said illustrative window so as to protect said dental care set from being directly accessible from an exterior of said housing through said illustrative window, while allowing a user of to visually observe said dental care set through said illustrative window.

2. The dental care promotional kit, as recited in claim 1, wherein dental care set comprises a plurality of dental care accessories spacedly supported at said receiving cavity for performing a corresponding dental care procedure for a user.

3. The dental care promotional kit, as recited in claim 2, wherein said protective rack further has a plurality of protective compartments indently and spacedly formed thereon, wherein each of said dental care accessories is fittedly received in said corresponding protective compartment so as to be securely mounted and protected within said receiving cavity.

4. The dental care promotional kit, as recited in claim 2, wherein said housing is made of light-weight, flexible, durable and inexpensive material so that a user is able to retrieve said promotion tool and said dental care set with ease.

5. The dental care promotional kit, as recited in claim 3, wherein said housing is made of light-weight, flexible, durable and inexpensive material so that a user is able to retrieve said promotion tool and said dental care set with ease.

6. The dental care promotional kit, as recited in claim 2, wherein said housing has at least one opening formed thereon for communicating said receiving cavity with an exterior of said housing, wherein a user is able to access said receiving cavity through said opening.

7. The dental care promotional kit, as recited in claim 3, wherein said housing has at least one opening formed thereon for communicating said receiving cavity with an exterior of said housing, wherein a user is able to access said receiving cavity through said opening.

8. The dental care promotional kit, as recited in claim 5, wherein said housing has at least one opening formed thereon for communicating said receiving cavity with an exterior of said housing, wherein a user is able to access said receiving cavity through said opening.

9. The dental care promotional kit, as recited in claim 5, wherein said promotional member of said promotion tool is made of light-weight material so as to allow easy carrying and inexpensive manufacturing, wherein promotional materials are printed on said promotional section of said promotional member while said reflective element is attached on said promotional member such that when said promotional member is taken out from said receiving cavity, said reflective element is still attached on said promotional member for providing reflective image to said user for an extended period of time.

10. The dental care promotional kit, as recited in claim 8, wherein said promotional member of said promotion tool is made of light-weight material so as to allow easy carrying and inexpensive manufacturing, wherein promotional materials are printed on said promotional section of said promotional member while said reflective element is attached on said promotional member such that when said promotional member is taken out from said receiving cavity, said reflective element is still attached on said promotional member for providing reflective image to said user for an extended period of time.

* * * * *